United States Patent [19]

Viles et al.

[11] Patent Number: 4,675,002
[45] Date of Patent: Jun. 23, 1987

[54] LIVER ASSIST DEVICE EMPLOYING TRANSFORMED CELL LINES

[76] Inventors: Joseph M. Viles, 2407 Knapp St., Ames, Iowa 50010; Paul V. Hart, Rte. 1, Lawson, Mo. 64062

[21] Appl. No.: 803,564

[22] Filed: Dec. 2, 1985

[51] Int. Cl.⁴ ............................................ A61M 37/00
[52] U.S. Cl. ....................................................... 604/5
[58] Field of Search ............ 604/5, 29; 128/DIG. 13; 210/321.1, 637–646, 321.2, 321.3, 321.4

[56] References Cited

U.S. PATENT DOCUMENTS

| 4,229,290 | 10/1980 | Raj | 604/5 X |
| 4,514,295 | 4/1985 | Mathieu et al. | 604/5 X |
| 4,596,549 | 6/1986 | Minami | 604/5 |

FOREIGN PATENT DOCUMENTS

| 871264 | 5/1971 | Canada | 604/5 |
| 2832870 | 2/1980 | Fed. Rep. of Germany | 604/5 |

*Primary Examiner*—John D. Yasko
*Attorney, Agent, or Firm*—Schmidt, Johnson, Hovey & Williams

[57] ABSTRACT

An improved extracorporeal liver assist device and method is provided which employs a blood perfusion membrane cultured with initially transformed hepatocytes until a confluent monolayer is developed, whereupon the hepatocytes are reverted to the somatic phenotype for perfusion purposes. Use of transformed hepatocytes permits serial subculturing to maintain a clinical supply of cells for the patient, while the in vitro proliferation characteristics and loss of contact inhibition of the transformed hepatocytes ensures rapid cell division and layer formation on the perfusion membranes. Virally transformed, temperature sensitive hepatocytes are preferred so that reversion of the cells can be accomplished by temperature change. The transformed hepatocytes may be cultured on the exterior surfaces of multiple capillary membrane cartridges, and subsequently reverted by elevating the temperature thereof. During perfusion, the patient's blood is passed through the lumen of the capillaries, and dissolved molecular species (e.g., bilirubin) diffuse through the membrane to be taken up and metabolized by the hepatocytes. Bathing solution is simultaneously passed around the exterior of the capillary tubes to remove metabolic wastes from the hepatocytes.

11 Claims, 3 Drawing Figures

LIVER ASSIST DEVICE EMPLOYING TRANSFORMED CELL LINES

BACKGROUND OF THE INVENTION

1. Field of the Invention

The present invention is broadly concerned with improved extracorporeal liver assist devices and methods designed to support a human or animal patient suffering from hepatic failure or insufficiency. More particularly, it is concerned with such an assist device designed for perfusion of the patient's blood, and wherein use is made of a semipermeable membrane supplemented with transformed hepatocytes subsequently reverted to the somatic phenotype thereof.

2. Description of the Prior Art

The progress of medical science has in recent years resulted in considerable research in the area of artificial organs. To give but one example, artificial kidney dialysis machines are now relatively commonplace, and are routinely used in cases of renal failure. In such machines, blood is withdrawn from a patient and passed through a dialysis chamber along with a dialysate; impurities within the patient's blood would normally be removed by the patient's kidneys diffused through the semipermeable membranes of the dialysis chamber, and are removed by the dialysate.

It has also been proposed in the past to provide an extracorporeal liver assist device to support patients suffering from hepatic failure. See, for example, Wolf et al., "Bilirubin Conjunction by an Artificial Liver Composed of Cultured Cells and Synthetic Capillaries", Trans. Amer. Soc. Artif. Int. Organs (1975), pages 16–27. In the Wolf et al. procedure, hollow fiber semipermeable membrane shell and tube cartridges are employed as an artificial liver. Such devices include a plurality of elongated tubular semipermeable membrane capillaries encased within a surrounding shell. Wolf et al. made use of primary hepatocytes cultured onto the exterior surfaces of the capillary membranes to form a solid tissue mass about the capillaries which is morphologically similar to the in vivo organization of hepatocytes in normal liver. These primary hepatocytes grown on hollow fiber capillaries demonstrated the ability to perform complex functions such as bilirubin uptake conjugation and secretion which are characteristic of normal liver in situ in a living animal.

A number of other cell types have been successfully grown on hollow fiber capillaries, e.g., Chinese hamster ovary cells, monkey kidney cells, embryonic fibroblasts from chicks and mice, Chang hepatoma cells, W138 cells and virally transformed hamster embryo fibroblasts. In addition, the assumption of organ function by cells grown on hollow fiber capillaries have been investigated by Chick et al. (Science 187: 847–848 (1975); Trans. Amer. Soc. Artif. Int. Organs 21: 8–15 (1975)). This work has demonstrated the long term maintenance of pancreatic beta cells on hollow fiber capillaries and the continued production of insulin by these pancreatic beta cells for the period of in vitro culture.

The specific literature describing such prior work, as well as other literature of background interest, includes:

Knazek, R. A. (1974). Fed. Proc. Fed. Am. Soc. Exp. Biol. 33: 1978–81.

Knazek, R. A.; Gullino, P. M.; Kohler, P. O; and Dedrick, R. I. (1972). Science 178: 65–67.

Knazek, R. A.; Kohler, P. O.; and Gullino, P. M. (1974). Exp. Cell Res. 84: 251–254.

Knisely, M. H.; Reneau, D. D.; and Bruley, D. F. (1969). Angiology 20: 1–56.

Kruse, P. F.; and Miedema, E. (1965). J. Cell. Biol. 27: 273.

Nettesheim, P.; and Makinodan, T. (1967). In "Methods in Developmental Biology." p. 471. Crowell-Collier, New York.

Rose, G. G. (1967). J. Cell. Biol. 32:108.

Russ, M. B. (1976). M. S. Thesis, University of Delaware, Newark.

Schratter, P. (1974). "Synthetic Capillaries for Cell Culture". Am. Lab., October: 33–38.

Schratter, P. (1976). "Cell Culture With Synthetic Capillaries". Methods in Cell Biol. XIV: 95 Thomlinson, R. H. and Gray, L. M. (1955). Br. J. Cancer 16: 841.

Tromwell, O. A. (1958). Exp. Cell Res. 16: 118–147.

White, A.; Handler, P.; and Smith, E. L. (1973). In "Principles of Biochemistry", 5th ed. p. 905. McGraw-Hill, New York.

Wolf, C. F. W. (1978). Intern. J. of Art. Organs. 1: 45–51.

While liver assist devices of the type described by Wolf et al. have shown some promise, a number of very significant problems remain which have precluded the widespread use of such techniques on a clinical basis. As noted, Wolf et al. made use of primary hepatocytes. These cells will not normally divide, and therefore cannot be carried in serial subculture. As a consequence, any clinical use of a Wolf et al. liver assist device would require a continuing supply of primary hepatocytes. When it is borne in mind that such hepatocytes should preferably be taken from the same species as patient, and should moreover be histo-compatible with the specific patient being treated, it will become apparent that the requirement for a continuing supply of primary hepatocytes presents a formidable if not insurmountable obstacle to repeated use of such liver assist device.

There is accordingly a decided need in the art for an improved liver assist device and method which provides needed liver function for patients suffering from hepatic failure while overcoming the practical problems associated with proposals making use of primary hepatocytes cultured onto semipermeable membranes.

SUMMARY OF THE INVENTION

The present invention largely overcomes the problems noted above, and provides a greatly improved liver assist device having production and operational characteristics making it extremely useful for ongoing, clinical treatment of patients suffering from hepatic failure of insufficiency.

Broadly speaking, the present invention is based upon the principle of utilization of initially transformed heptocytes cultured onto a perfusion membrane, and then reverted to the somatic phenotype thereof. Use of transformed hepatocytes in this fashion takes advantage of certain known properties of such transformed cells, i.e., their ability to be serially subcultured in vitro virtually forever, and the characteristic high proliferation rate and loss of contact inhibition common to such cells. In particularly preferred forms, use is made of virally transformed cells which are temperature sensitive. Papovavirus species such as Simian Virus 40 (SV40) are particularly preferred for hepatocyte transformation. The temperature sensitivity of the transformed heptocytes also permit reversion to the somatic state by the simple expedient of elevating the hepatocytes a few degrees (e.g., from 37° to 41° C.).

Initially transformed hepatocytes are cultured onto one face of a semipermeable membrane. In preferred forms, a plurality of interconnected, tube and shell multiple hollow capillary membrane cartridges are employed, and the transformed hepatocytes are cultured on the exterior surfaces (i.e., the shell side) of the capillary membranes. Such culturing involves an initial inoculation of the cartridge(s) followed by circulation of an appropriate growth medium through the shell side thereof until a confluent monolayer of transformed hepatocytes is developed. At this point, the temperature of the circulating growth medium is elevated (and the entire tube and shell membrane device may be placed bodily within a temperature regulated warming water bath) in order to thermally shock the transformed hepatocytes and cause reversion thereof to the somatic phenotype. Thereafter, cell division (proliferation) ceases, and the cultured cartridges are ready for use as an extracorporeal liver assist device.

In the blood perfusion protocol, the patient's blood is withdrawn and passes into contact with the face of the semipermeable membrane remote from the hepatocyte layer. In the preferred form of the invention, this involves passing the patient's blood through the lumen of the plural hollow fiber capillaries. During such passage, molecular species dissolved in the patient's blood (such as bilirubin) diffuse through the semipermeable membrane capillaries and are then taken up and metabolized by the hepatocyte layer. This in turn causes excretion of metabolyzed waste from the hepatocytes which is removed by a countercurrently circulating bathing fluid circulated through the shell side of the cartridges.

In keeping with the foregoing procedure, the overall liver assist device includes, in addition to the cultured membrane cartridges or their equivalent, means for passing the patient's blood in serial fashion from the patient into and through the perfusion cartridges, and also a second fluid loop for passage of bathing fluid into and through the shell sides of the cartridges in order to remove wastes therefrom.

DESCRIPTION OF THE PREFERRED EMBODIMENTS

Figure 1:
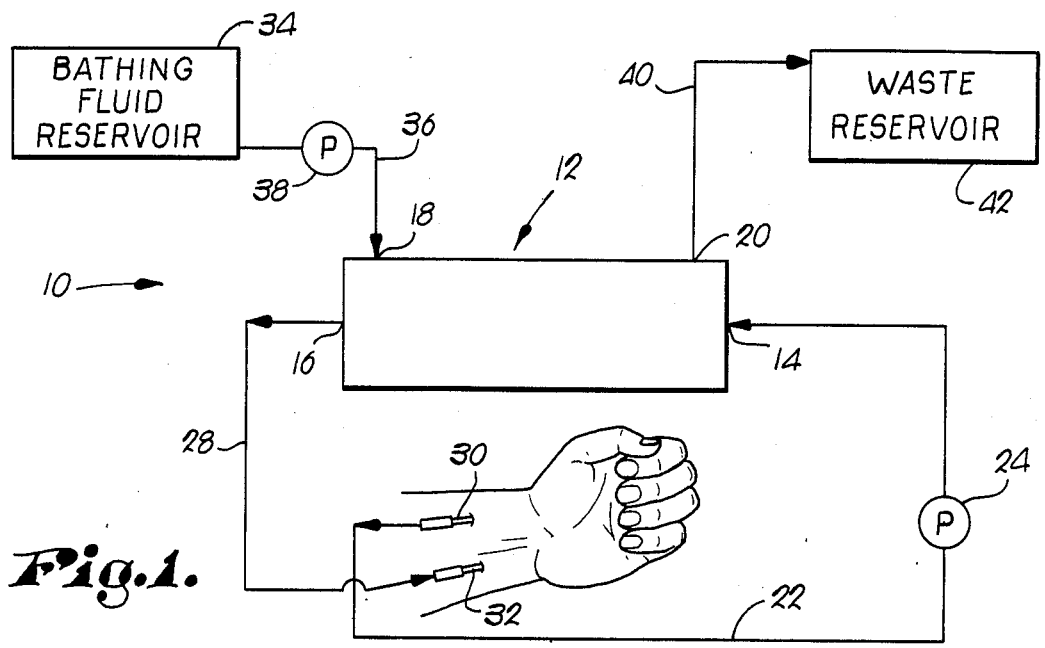
FIG. 1 is a schematic representation of an overall liver assist device in accordance with the invention, shown operatively connected to a patient during a liver assist treatment.

The concept of cell transformation is in general well known, and is usually defined operationally, i.e., in terms of the properties of the cells after alteration by a transformant. In the case of transformations induced by oncogenic viruses, the characteristics of transformed cells include the following: (Enders "Cell Transformation by Viruses As Illustrated by the Response of Human and Hamster Renal Cells to Simian Virus 40", *Cell Transformation*, page 113–152):

1. Altered growth pattern, i.e., loss of contact inhibition.
2. Altered morphology.
3. Increased growth rate.
4. Increased capacity to persist in serial subcultures.
5. Altered metabolism.
6. Chromosomal abnormalities.
7. Reduced capacity to support multiplication of infectious virus.
8. Increased resistance to reinfection with the transforming agent as well as certain other viruses.
9. Emergence of new cellular antigenic components.
10. Capacity to form neoplasms.

In addition, the most preferred transforming virus in accordance with the present invention, SV40, induces the following particular properties in transformed cells (*Molecular Biology of Tumor Viruses*, Part 2: *DNA Tumor Viruses*, John Tooze, Editor, Cold Spring Harbor Monographs, 10B (1980), Library of Congress Accession No. QR 372 06 M64 1980 Part 2):

Growth high or indefinite saturation density[a]
different, usually reduced, serum requirement[a]
growth in agar or methocel suspension-anchorage independence[a]
tumor formation upon injection into susceptible animals
not susceptible to contact inhibition of movement
growth in a less-oriented manner[a]
growth on monolayers of normal cells[a]

Surface increased agglutinability of plant lectins[a]
changes in composition of glycoproteins and glycolipids
tight junctions missing
fetal antigens revealed
virus specific transplantation antigen
different staining properties
increased rate of transport of nutrients
increased secretion of proteases or activators[a]

Intracellular disruption of the cytoskeleton
changed amounts of cyclic nucleotides

Evidence of virus virus-specific antigenic proteins detectable
viral DNA sequences detected
viral mRNA present
virus can be rescued in some cases Transformed cells show many, if not all, of these properties, which are not shared by untransformed parental cells.
[a]Several of these properties have formed the basis of selection procedures for isolating transformants.

For purposes of the present invention, the term "transformed hepatocyte" is defined as primary hepatocytes which have been treated with a transformant and which exhibit at least the following properties:
(1) Increased capacity to persist in serial subcultures;
(2) Increased growth rate in vitro; and
(3) Loss of contact inhibition.

While a wide variety of transformants can be employed to achieve transformation, it is preferred to make use of viral transforming agents in accordance with the present invention. The papovavirus group, and particularly SV40, is preferred as a transforming agent. Human cells are semipermissive of SV40 infection, that is, they can be infected and they support viral replication, but they do not all complete the lytic cycle. The survivors of the lytic cycle are transformed and exhibit the desired growth characteristics; however, they do continue to release SV40 virions after months of culture. SV40 has a much more restricted oncogenic potential than other papovaviruses. Considering the history of the exposure to SV40, it would seem probable that it is not oncogenic in humans, and indeed to date the only reported case of SV40 associated human disease is a single case of malignant melanoma. A wide variety of attenuated SV40 mutants are available, particularly group A mutants which are defective in early gene (A) function; they induce SV40 T antigen synthesis and stimulate the replication of host cell DNA, but fail to produce any viral DNA or capsid antigens under certain experimental conditions. These mutants in the (A) gene region produce a heat labile T antigen, necessary to maintain transformation, which ceases to function at elevated temperatures. Transformation by these temperature sensitive SV40 mutants is therefore reversible by simply increasing the temperature of the culture. When the temperature is elevated, the transformed cells cease to produce SV40 viral DNA or SV40 capsids, lose their transformed characteristics, and revert to the original somatic phenotype. Transformation with temperature sensitive SV40 thus permits switching from the transformed phenotype back to the somatic phenotype by elevating the temperature a few degrees; this then allows the utilization of the proliferation rate of the transformed state to grow rapidly large area confluent monlayers on a semipermeable membrane substrate, whereupon virus production can be stopped and reversion effected to the somatic phenotype for metabolic perfusions.

Transformation of hepatocytes using viral agents such as SV40 is accomplished using known techniques. Broadly speaking, primary hepatocyte cultures are enzymatically dispersed and cultured, followed by infection with the viral transformant. Thereafter, the transformed hepatocytes are serially subcultured to select the stably transformed cells from abortive or transiently transformed cells. The stable cells are then used to establish a line for clinical use. Specific details of a preferred transformation procedure are set forth in the following Example.

After a stably transformed cell line has been established, the cells can be cultured onto semipermeable membranes to form a liver assist device. Here again, the specific details of such a colonization procedure are within the skill of the art, and an exemplary method is set forth in the Example.

The most preferred membrane structure for use in connection with the present invention comprises a plurality (usually three) of upright tube and shell cartridges containing an outermost tubular shell along with a plurality of vertically oriented synthetic resin capillaries within each shell. Appropriate sealing structure is provided for maintaining the shell side of the cartridges (i.e., exteriorly of the capillaries) physically separate from the lumen or interior of the capillaries. Further, appropriate input and output ports are provided for continuous flow of respective fluids through the tube and shell portions of the cartridges.

One particularly preferred apparatus of the type described is produced by the Amicon Corporation, Scientific Systems Division, of Danvers, Mass. as Model "DC30." This device is described in a technical bulletin published by Amicon Corporation entitled "High-Yield Hollow Fiber Concentration/Dialysis System for Rapid Processing of Macromolecular Solutions DC30"; this bulletin is hereby expressly incorporated by reference into the present application. The Model DC30 device comprises three upright tube and shell cartridges of the type described, together with appropriate and fluid control devices. The Amicon devices can be provided with various types of internal capillaries, in terms of their exclusion limit, which effectively limits the size of molecules permitted to diffuse through the capillary walls. For purposes of the present invention, the hollow fiber capillaries should have an exclusion limit of between 30,000 and 50,000 daltons, with the lower limit being preferred.

Turning now to the drawing, an overall liver assist device 10 in accordance with the invention is schematically depicted in FIG. 1. The device 10 includes a membrane assembly broadly referred to by the numeral 12, providing a blood input 14, a blood output 16, a bathing solution inlet 18 and a bathing solution outlet 20. The device 12 further includes at least one semipermeable membrane capable of supporting hepatocytes prepared in accordance with the methods of the present invention. In addition, the assembly 12 is provided with respective flow paths for the blood and bathing solution, which paths are separated by the described membrane.

The device 10 further includes a blood input line 22 which is operatively coupled to assembly input 14, and includes a conventional pump 24. A blood output line 28 is also provided as illustrated. Input line 22 and output line 28 are operatively connected to appropriate arterial-venous fistulas 30, 32 implanted into the forearm of a patient (line 22 thereby being coupled to the radial artery of the patient, whereas line 28 is coupled to the forearm vein). Of course, other arterial-venous connections to the patient could be fashioned, depending upon the discretion of the treating physician.

The device 10 further includes a bathing fluid reservoir 34 with a solution input line 36 connected thereto and coupled to input 18. A conventional pump 38 is interposed within line 36 for purposes of circulating fluid through assembly 12. A solution output line 40 is operatively coupled between output 20 and a waste reservoir 42 as illustrated.

Figure 2:
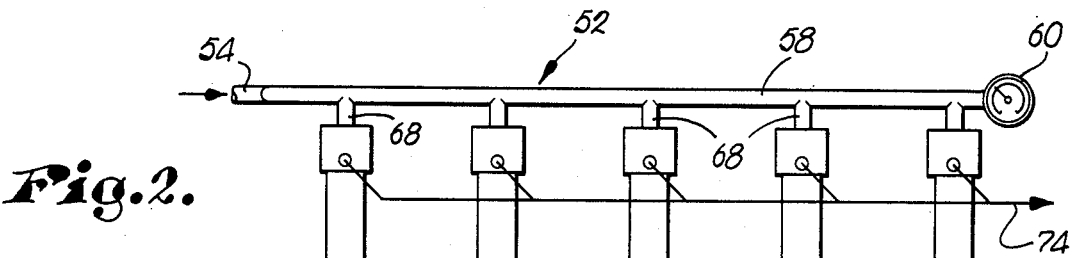
FIG. 2 is a partially schematic side view illustrating the construction of a preferred multiple-cartridge liver assist perfusion assembly.
Figure 3:
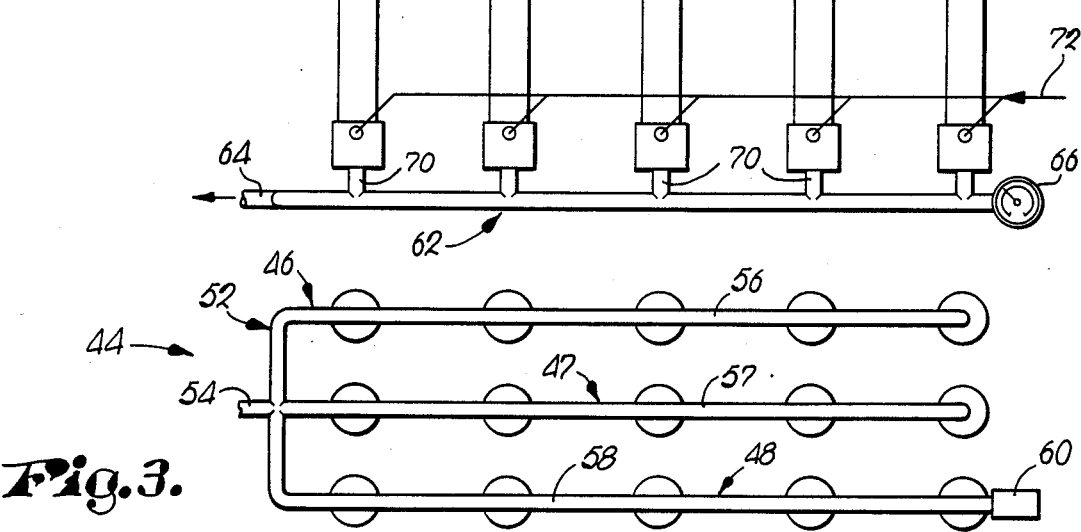
FIG. 3 is a plan view of the chamber depicted in FIG. 2.

Attention is next directed to FIGS. 2–4, which illustrate a modified membrane assembly broadly denoted with the numeral 44. It is to be understood in this respect that the assembly 44 could be used in the overall system 10, and in that event would function as the schematically depicted assembly 12. In any event, the assembly 44 comprises three banks 46, 47 and 48 each containing five upright tube and shell hollow capillary cartridges 50. Each of these cartridges is identical and includes a large number of hollow fiber capillaries therewithin; the preferred cartridges are Amicon ® units having a 30,000 dalton exclusion limit. The assembly 44 further includes a trifurcated input header 52 having a common blood input line 54 and branch lines 56, 57 and 58 respectively operatively coupled to and feeding the upper ends of the cartridges 50 in each bank 46, 47 and 48. A pressure gauge 60 is operatively connected to the end of branch line 58 remote from input 54, in order to facilitate monitoring of the pressure conditins within the assembly. A similar trifurcated blood output header 62 is located adjacent the bottoms of the respective cartridges 50, and is operatively connected to each bank thereof in the same manner as input header 58. The header 62 includes a common blood output line 64 as illustrated, and a pressure gauge 66 coupled to the branch thereof associated with bank 48. The input and output headers 52 and 62 are operatively connected to short input and output pipes 68, 70 to the lumen or interior of the hollow fiber capillaries contained within each cartridge 50. Thus, blood from a patient passes through input 54 and the branches 56, 57 and 58 for passage downwardly through the lumen of the capillaries contained within the respective cartridges 50, whereupon such blood passes outwardly through the pipes 70 for return to the patient through header 62 and output line 64.

The overall assembly 44 also includes a bathing solution input line 72 which is likewise of trifurcated construction, and is in turn operatively connected to each of the cartridges 50 of the separate banks 56, 57 and 58. It will be noted in this connection that the line 72 is connected to the cartridges 50 adjacent the lower ends thereof. Output for the bathing solution is provided by means of an output line 74 adjacent the upper ends of the cartridges 50 and operatively connected to each of the latter. By virtue of the construction of the input and output lines 72, 74, it will be seen that bathing solution is passed in countercurrent relationship to the blood flowing through the assembly. In addition, the lines 72, 74 are coupled to the shell sides of the respective cartridges 50, i.e., so that bathing solution passes through the cartridges exteriorly of the tubular capillaries.

In the use of assembly 44, the line 54 would be operatively connected to the artery of a patient, whereas the line 64 would be connected to an appropriate vein. The pump 24 associated with the overall apparatus would then be activated, in order to withdraw blood from the patient and pass the same through the assembly, with blood flow being from top to bottom. At the same time, bathing solution from reservoir 34 would be passed through the shell sides of the respective cartridges in countercurrent relationship to the blood flow, i.e., from bottom to top. For this purpose, pump 38 would be activated.

The following Example sets forth the presently preferred details of the invention in terms of preparation and use of the liver assist device.

EXAMPLE

In this example, a liver assist device is prepared which includes a plurality of hollow fiber tubes defining semipermeable membranes having confluent monolayers of hepatocytes on the extenious surfaces thereof.

In the first step, host cell hepatocytes are prepared from donor liver tissue derived from biopsy or autopsy specimens. Advantageously, the liver tissue is human, and is histocompatible with the ultimate patient to minimize any possible immune response problems during subsequent perfusion procedures.

Primary hepatocyte cultures are prepared by enzymatically dispersing the solid liver tissue by a modification of the collagenase digestion described by Seglen, *Methods in Cell Biology*, Vol. XIII. Tissue blocks of 1 mm. cubed, derived by mincing larger samples, are immersed in 20 ml. of $Ca^{2+}$-free buffer (Buffer I, Table 1) containing 0.5 mM EGTA and incubated at 41° C. with agitation for 10 minutes. The EGTA-buffer solution is then decanted and the tissue rinsed several times with wash buffer (Buffer III, Table 1). 20 ml. of standard buffer containing 0.05% collagenase (Sigma, Type IV) with 10 mM $Ca^{2+}$ (Buffer II, Table 1) is then added and the tissue incubated with agitation for 60 minutes at 41° C. Dissociated cells are then drawn off by pipette at 10 minute intervals and deposited in an iced 250 ml. flask. An additional 20 ml. of dissociation medium is then added to the remaining undissociated tissue after each interval and incubation with agitation continued. Two ml. of FCS (Fetal Calf Serum) is added to the suspension of cells after each aliquot of dissociated cells is collected.

After dissociation of the tissue, the cell suspension is filtered through sterile nylon stocking and divided equally into two 50 ml. sterile centrifuge tubes. The cells are centrifuged for two minutes at 50 g, the dissociation medium decanted and a 10 ml. aliquot of wash buffer (Buffer III, Table 1) with 10% FCS added to the centrifuge tube. The pelleted cells are gently resuspended and centrifuged again for two minutes at 50 g. The supernatant is decanted and the cells resuspended again in 10 ml. wash buffer (Buffer III, Table 1). A 0.1 ml. aliquot is withdrawn and added to 0.8 ml. of wash buffer (Buffer III, Table 1) and 0.1 ml. 0.4% trypan blue dye. A sample is placed on a hemocytometer and the number of viable (gold) cells and the number of nonviable cells (blue) determined. Cell yield and percentage viability are calculated. The remainder is centrifuged for two minutes at 50 g, the supernatant decanted and sufficient Liebowitz L-15 medium with 10% FCS added to yield a dilution of $4-5 \times 10^6$ viable cells per 3 ml. The pelleted cells are gently resuspended in this medium and aliquots transferred to plastic petri dishes.

Plastic tissue culture dishes (60 mm.) inoculated with 3 ml. of the suspension (about $4 \times 10^6$ viable cells) are allowed to incubate at 37° C. in a humidified (i.e., saturated) air environment. During this incubation period a proportion of the inoculated cells attach to the dish walls; after incubation, unattached cells are discarded by pouring off the medium. A fresh aliquot of 3 ml. of the Leibowitz L-15 medium with 10% FCS is added to each dish and the cultures are incubated an additional 24 hours under the same conditions as the initial incubation; during this second incubation the attached cells flatten into a monolayer.

The cultured monolayers of primary hepatocytes are then superinfected with tsA28 SV40 virus ($10^6$–$10^7$ virus particles per cell) suspended in Liebowitz L-15 medium with 10% FCS added. After 90 minutes incubation at 37° C. for virus attachment in the humidified air environment described previously, the unattached viruses are poured off and fresh aliquots (3 ml.) of the Liebowitz L-15 medium supplemented with 10% FCS are added to each dish. The cells are then kept in culture with fresh aliquots (3 ml.) of the described medium added every 24 hours until the foci of transformed cells begin to appear, which usually will take about 1 week.

Upon identification of plaques of transformed cells, the clones are dispersed with trypsin and are serially subcultured using conventional techniques to select out the stably transformed cells (i.e., those which possess the capacity to persist in prolonged serial subculture) from the abortive, or transiently transformed cells. The stably transformed cells are then used to establish a cell line of high growth and division rates with reduced requirements (1%) for FCS concentration in the growth medium. If desired, continued shedding of SV40 virions may be suppressed by culturing the stably transformed cells in the L-15 medium supplemented with anti-SV40 serum derived from animals immunized to SV40.

The stably transformed cell lines are essentially immortal and can be maintained indefinitely in cell culture. When it is desired to produce a liver assist device, the transformed cell line is used to inoculate hollow fiber tube bundles; the method of Wolf et al., "Bilirubin Conjunction by an Artificial Liver Composed of Cultured Cells and Synthetic Capillaries", *Trans. Amer. Soc. Artif. Int. Organs,* (1975, pages 16-27) may be employed for this purpose. The Wolf et al. paper is expressly incorporated herein by reference.

Basically, the technique involves a circumfusion procedure wherein the selected tube and shell semipermeable membrane cartridge(s) such as those described above are sterilized, and the primary hepatocytes inoculated (e.g., $10^4$–$10^7$ cells) into the shell side of each of the cartridge(s) i.e., for growth on the exterior surfaces of the semipermeable tubes). Thereupon, an appropriate growth medium for the transformed hepatocytes is circulated through the shell sides of the seeded cartridge(s) for growth-promoting contact with the hepatocyte. In practice, the Amicon ® hollow fiber cartridge described above are employed, with the inner hollow fiber tubes having an exclusion limit of 30,000 daltons in order to prevent exchange of released SV40 virions into the inner capillary lumen and prevent exchange of blood proteins and hepatocyte-secreted proteins across the capillary membrane barrier. Rigorous separation of virions and dissolved proteins by careful selection of exclusion limits of the capillary membrane reduces the possibility of virus transmission to the patient and any patient immune responses to the host hepatocytes.

Upon inoculation and during the circumfusion procedure, the transformed hepatocytes colonize the outside of the hollow fiber capillaries. Advantageously, each cartridge is inoculated with from $10^4$–$10^7$ hepatocytes, and the circulating growth medium employed is Leibowitz L-15 medium supplemented with 1% fetal calf serum maintained at temperature of 37° C. When a confluent monolayer is established (usually following from about 1 to 8 days growth medium circulation the incubation temperature is raised to 41° C. by elevation of the temperature of the circulating growth medium and immersion of the tube and shell device into a warming water bath maintained at 41° C. This causes the transformed cells to revert to the somatic phenotype, cease virus replication, cease cellular DNA replication, and resume contact inhibition characteristics. The amount of time needed to achieve a confluent monolayer basically depends upon the size of the inoculum. The maximum density to which TsA28 SV40 transformed human cells will proliferate is about 120,000 cells/cm$^2$, and this density can normally be achieved in about 6 days with an inoculum of 4,000 cells/cm$^2$. The number of cells in the inoculum is determined by the total surface area of the capillary fibers and the time required to reach maximum density is determined by the number of cells in the inoculum. For an Amincon capillary fiber cartridge with a total surface area of 9,000 cm$^2$ an inoculum of a total of $5 \times 10^7$ cells, assuming a 40% plating efficiency, will yield a usable device after 6 days of incubation. Doubling the size of the inoculum will reduce incubation time by about 1 day. A four-fold increase in the size of the inoculum will reduce incubation time by about another day. The maximum density noted above represents a condition of an overgrown monolayer, the confluent monolayer being a minimal acceptable configuration; an overgrown monolayer, i.e., two or more monolayers thick would be an ideal condition, particularly since nutrient media, i.e., Leibowitz L-15 and the patient's blood, would bath opposite side of the cell layer. This stable, confluent monolayer of somatic phenotype hepatocytes grown on the hollow fiber capillary substrate can then be used to supplement liver function by perfusion of the patient's blood through the capillary fiber lumen.

The specific most preferred inoculation protocol is set forth below:

1. Flood the extracapillary spaces of sterilized Amicon ® cartridges each having a 30,000 dalton exclusion limit with Leibowitz L-15 medium with 1% FCS until the cartridges are full, that is no air bubbles.

2. Add inoculum of $5 \times 10^7$ transformed hepatocytes per cartridge to the flooded extracapillary spaces.

3. Agitate gently to evenly distribute the suspended cells throughout the capillary outer surfaces and then allow the cells to settle on the surfaces.

4. After four hours place the cartridges on a roller rack and revolve the cartridges very slowly at 1 RPM to redistribute unattached cells over the capillary outer surfaces. The rate of rotation should be decreased to 1/5 RPM gradually over a twenty hour period.

5. Following this twenty-four hour initial period of attachment, the cartridges can be removed from the roller rack and connected to a large reservoir of Leibowitz L-15 medium with 1% FCS and a pump to circulate the medium through the extracapillary spaces.

6. An additional inoculum of $5 \times 10^7$ transformed hepatocytes per cartridge is then added to the flooded extracapillary spaces and agitated gently to evenly distribute the suspended cells throughout the capillary outer surfaces. Following a four hour settling and attachment period, the pumping system will be used to circulate slowly the medium from the reservoir through the extracapillary spaces.

7. The pumping system will then continuously recirculate the medium for an additional five days at about 500 ml/minute, during which time colonization of the outside of the entire surface area of the hollow fiber capillaries will occur and a confluent monolayer of transformed hepatocytes will cover all of those surfaces. Specifically, this medium should be circulated at a rate of 0.06 ml/min/cm$^2$ (capillary surface area), i.e. about 500 ml/min for each HP10 cartridge. Simultaneously an identical solution should be counter currently circulated through the capillary lumen at the same flow rate.

8. The cartridges are then placed in a 41° C. water bath and the growth medium is circulated through the extracapillary spaces of the cartridge at 41° C. to revert the hepatocytes to the somatic phenotype thereof. After a further 24 hours, the Leibowitz L-15 with 1% FCS and 5 mg % (5 mg/100 ml) bilirubin is pumped at 0.06 ml/min/cm$^2$ through the capillary lumen. This provides the newly reverted hepatocytes a substrate to conjugate; the shell side bathing medium could then be analyzed for the presence of bilirubin conjugates to determine efficacy of the metabolic assist function. Once determination of functionality is made, the capillary lumen are then flushed with buffered saline to ready the cartridges of use; these are advantageously interconnected to form a plural cartridge device of the type described.

In the perfusion procedure, steps are first taken to avoid coagulation of the patient's blood in the assist device. In patients without hepatic failure coagulopathy, heparinization is established by injection of an initial dose of 300 units/Kg of body weight of heparin. During perfusion, additional heparin titration may be used if necessary to keep the activated clotting time greater than 400 seconds. Just prior to the discontinuance of perfusion, protamine sulfate is injected to reverse the heparinization. In patients with a coagulopathy (secondary to hepatic failure) or who have had recent abdominal surgery, regional heparinization may be used. In this procedure, heparin is added to the afferent loop of the liver assist device tubing for anticoagulative purposes, with the addition of protamine sulfate to the efferent loop to effect reversal.

The actual perfusion protocol is established using techniques similar to conventional bypass perfusion. Silicon rubber tubular shunts are operatively placed between the radial artery and vein to establish intraluminal blood flow rates of up to 350 cc/min. Arterial-venous fistuals, fashioned surgically by side-to-side anastamosis of the radial artery and forearm vein may also be used, after adequate maturing of the surgical anastomosis.

For most perfusion of humans, blood flows of from about 100 to 350 cc./min. are adequate through the extracorporeal liver assist device of the invention. Such blood flow is directed through the lumen of the membrane tubes, (i.e., through the tube side of the cartridge(s)) for contact with the faces of the membrane tubes remote from the hepatocyte layers. Typically, a supplementary liver function perfusion should involve blood flow through the device for a period of from about 4 to 10 hours, three to five times weekly.

Simultaneously with blood flow through the device, a bathing solution is concurrently passed through the shell sides of the cartridge(s) for contact with the hepatocytes. This bathing solution is preferably Leibowitz L-15 medium supplemented with 1% fetal calf serum, and maintained at a temperature of about 41° C.

During perfusion, molecules such as bilirubin dissolved in the patient's blood will diffuse through the capillary membranes to the hepatocyte layers simultaneously with nutrients from the blood. The bilirubin and other molecular species will then be available for takeup and metabolism (conjugation in the case of bilirubin) and consequent excretion of wastes by the hepatocytes into the shell sides of the cartridge(s). Hence, the cultured hepatocytes will assume the complex functions ordinarily provided by the normal liver in vivo.

In addition to supplementation of general liver function in case of chronic liver failure, additional uses could include alleviation of the clinical symptoms associated with a wide variety of inherited metabolic diseases such as familial hyperchloesterolemia, generalized gangliosidoses and other storage diseases akin to Tay-Sach's syndrome, and I cell disease by providing additional unimpaired metabolic capacity to offset metabolic capacity lost to genetic lesions.

TABLE I

Composition of Buffers Used for Collagenase Digestion[1]

| | Buffer | | |
|---|---|---|---|
| | I $Ca^{2+}$-free buffer | II Collagenase buffer | III Washing buffer |
| NaCl | 8,000 | 8,000 | 8,000 |
| KCl | 400 | 400 | 400 |
| $CaCl_2 \cdot 2H_2O$ | — | 1,000 | 180 |
| HEPES | 2,400 | 2,400 | 2,400 |
| Streptomycin | 100 | 100 | 100 |
| Penicillin | 60 | 60 | 60 |
| Glucose | 1,000 | 1,000 | 1,000 |
| EGTA | 192 | — | — |
| Collagenase | — | 500 | — |

[1] Salt concentrations are given in milligrams per 1000 ml. of final solution, pH was adjusted to pH 7.4 with 10N NaOH. All solutions were sterilized by filtration through a millipore membrane filter (0.22u).

We claim:

1. A method of extracorporeal blood processing in support of an organism suffering from hepatic failure or insufficiency, said method comprising the steps of:
   providing a semipermeable membrane presenting opposed first and second faces, with said first face having thereon a layer of initially transformed hepatocytes reverted to the somatic phenotype thereof;
   withdrawing blood from said organism;
   passing said withdrawn blood into contact with said second membrane face, and causing molecules dissolved in the blood to diffuse through the membrane and contact said hepatocytes for uptake and metabolic processing of said molecules, and consequent excretion of metabolized wastes from the hepatocytes; and
   during said blood passing step, passing a bathing solution into contact with said transformed hepatocyte layer for removal of said excreted metabolic wastes.

2. The method of claim 1, said hepatocytes being temperature sensitive for reversion to the somatic phenotype thereof by raising the temperature of the hepatocytes.

3. The method of claim 2, said hepatocytes being virally transformed.

4. The method of claim 3, said hepatocytes being of human origin, and being virally transformed by Simian Virus 40.

5. The method of claim 1, said membrane comprising a tube, said first face being the exterior face of the tube.

6. The method of claim 5, said membrane comprising a plurality of said tubes.

7. The method of claim 1, said blood withdrawal being at a rate of from about 100 to 350 cc/minute.

8. The method of claim 1, said bathing solution being passed in countercurrent relationship to said blood.

9. The method of claim 1, said bathing solution comprising Leibowitz L-15 medium supplemented with 1% fetal calf serum.

10. The method of claim 1, said layer being at least a confluent monolayer.

11. In a liver assist device for extracorporeal blood processing in support of an organism suffering from hepatic failure or insufficiency, said device including a semipermeable membrane presenting first and second opposed faces, a layer of hepatocytes on said first membrane face, and means for passing withdrawn blood from said organisms into contact with said second face while simultaneously passing a waste-removing bathing solution into contact with said hepatocytes, the improvement which comprises:
   employing as said hepatocyte layer primary hepatocytes which have been initially transformed to cause the hepatocytes to proliferate in vitro and decrease the contact inhibition thereof, followed by reversion of the transformed hepatocytes to the somatic phenotype thereof.

* * * * *